United States Patent [19]

Trevorrow

[11] 4,264,647
[45] Apr. 28, 1981

[54] REFERENCE ELECTRODE PRINTING PROCESS AND MASK FOR EXHAUST GAS OXYGEN SENSOR

[75] Inventor: John Trevorrow, Flint, Mich.

[73] Assignee: General Motors Corporation, Detroit, Mich.

[21] Appl. No.: 80,449

[22] Filed: Oct. 1, 1979

Related U.S. Application Data

[63] Continuation-in-part of Ser. No. 30,776, Apr. 17, 1979, abandoned.

[51] Int. Cl.³ .......................... B05D 5/12; B05C 3/02; B29F 1/10
[52] U.S. Cl. .................................. 427/125; 427/238; 427/282; 427/286; 427/287; 427/383.5; 427/376.6; 204/195 S; 118/406; 118/408; 118/421; 118/504; 425/110; 425/468; 425/469; 264/269; 264/516
[58] Field of Search ............... 427/238, 125, 282, 286, 427/287, 383.5, 376.6; 118/213, 421, 504, 505, 406, 408; 264/267, 268, 269, 516; 204/195 S; 425/110, 468, 469

[56] References Cited

U.S. PATENT DOCUMENTS

| | | | |
|---|---|---|---|
| 3,889,628 | 7/1975 | Usab | 118/3 |
| 3,978,006 | 8/1976 | Topp et al. | 252/477 R |
| 4,001,469 | 1/1977 | Harvey | 427/238 |
| 4,021,326 | 5/1977 | Pollner et al. | 204/195 S |
| 4,039,703 | 8/1977 | Kemijo et al. | 427/238 |
| 4,107,018 | 8/1978 | Bode et al. | 427/419 A |
| 4,169,778 | 11/1979 | Mann et al. | 204/195 S |

Primary Examiner—Ronald H. Smith
Assistant Examiner—Richard Bucker
Attorney, Agent, or Firm—Robert J. Wallace

[57] ABSTRACT

A reference electrode is rapidly automatically applied to the interior of tapered vitrified zirconia thimbles for an exhaust gas oxygen sensor. The coating is consistently smooth and predetermined in physical and electrical characteristics. In a specific example, a hollow elastomeric finger is nested within the thimble after dispensing a measured quantity of conductive ink into the thimble bottom. A gas jet applied to the ink from the finger lower end flows the conductive ink throughout a coating cavity below a shoulder in the finger after the ink quantity is substantially all applied to cavity walls, it no longer blocks a cavity vent, and allows the gas to flow freely through the cavity. Gas flow is then discontinued, and the finger withdrawn from the thimble.

7 Claims, 6 Drawing Figures

REFERENCE ELECTRODE PRINTING PROCESS AND MASK FOR EXHAUST GAS OXYGEN SENSOR

CROSS REFERENCE TO RELATED PATENT APPLICATION

This patent application is a continuation-in-part of United States patent application Ser. No. 030,776, filed Apr. 17, 1979, now abandoned.

FIELD OF THE INVENTION

This invention relates to a process for selectively applying a coating to the interior of a tapered ceramic cup and more particularly to a process for making an air reference electrode within a tapered vitrified zirconia thimble for an exhaust gas oxygen sensor, and to a deformable mask for use in such a process.

BACKGROUND OF THE INVENTION

One typical automotive-type solid electrolyte exhaust gas oxygen sensor is disclosed in U.S. Pat. No. 3,844,920 Burgett et al. In this typical structure the solid electrolyte is a zirconia body shaped as a tapered thimble. The interior and exterior of the thimble have separate porous electrode coatings of platinum or the like. The inner electrode is exposed to air for establishing reference potential. The outer electrode is exposed to the exhaust gas for establishing a potential determined by its oxygen concentration. In the past, the inner electrode covered the entire inner surface of the thimble. An improved configuration for the inner electrode is shown in United States patent application Ser. No. 961,137 entitled "Heated Solid Electrolyte Oxygen Sensor", filed Nov. 16, 1978, in the names of Gamdur S. Mann et al, now U.S. Pat. No. 4,169,778, and assigned to the assignee of this invention. In this improved configuration, the inner electrode covers only the bottom of the thimble. An electrode stripe extends up the side wall of the thimble to its top edge to facilitate making electrical contact with the electrode.

The inner electrode has heretofore been formed by painting on a coating of the platinum ink onto the inner surface of the zirconia thimble. Because of the small size of these thimbles, it has been difficult to brush the platinum ink onto their inner surfaces. In fact, it has been the practice of at least one manufacturer to apply this coating by means of pipe cleaners or the like. In any event, each zirconia thimble was individually handled and painted. Sometimes two coatings were required, which doubles the risk of contamination, damage, cost, etc. Also, hand painting produced electrodes that had properties varying from part to part, due to inconsistencies in thickness area, configuration, and other like variations. As a result, yields of acceptable parts were not very high, even though tolerances were set rather wide. I have found how to apply the electrode ink consistently, controllably and rapidly without human handling during the coating process. I have found how to automatically selectively coat the thimbles even though there is little room within their interior. Still further, I have been able to apply a highly uniform coating that is smooth and predictable in thickness and electrical resistance. High reproducibility in both physical and electrical characteristics are obtained in a single coating step that requires no human handling. Consequently, yields of acceptable products can be increased. It even appears that an improvement in sensor performance is achieved.

OBJECTS AND SUMMARY OF THE INVENTION

An object of this invention is to provide an improved process for selectively applying a coating to the interior of a tapered ceramic cup. More specifically it is an object of this invention to provide an improved process for applying an inner electrode on zirconia thimbles for an automotive-type exhaust gas oxygen sensor.

Another object of the invention is to provide a unique mask for selectively applying an inner electrode to the interior of a solid electrolyte cup.

Further it is an object of the present invention to provide an improved process of the above type wherein the mask is a hollow, deformable insert that has a taper slightly less than the thimble interior, an elastomeric circumferential shoulder for spacing the insert from the thimble bottom and closing an electrode cavity portion, a generally axially-directed slot for defining a cavity portion vent in conjunction with the zirconia thimble, and a path for applying gas pressure through the interior of the insert to the lowermost end of the cavity portion, so as to define a fluid flow path wherein the gas pressure drives a premeasured and predeposited electrode material up the sides of the cavity in a circumferentially uniform fashion to the insert shoulder and then up the axially-directed slot for substantially the entire axial length of the thimble interior exposed in the insert slot.

Still further it is an object of the present invention to provide a process for applying conductive coatings to the interior cavities of automotive-type zirconia exhaust gas sensors and a mask suitable for use therein, which lend themselves to high volume application of such coatings with significantly reduced human participation and significantly increased mechanization, provide high yields with a high degree of reproducibility in both the distribution and thickness of the electrode coating, and in other respects especially suitable for lower cost and practical manufacture of automotive-type zirconia exhaust gas oxygen sensors.

The invention comprehends applying an inner electrode ink to a tapered zirconia thimble by initially depositing in the thimble an amount of ink premeasured to be just sufficient for the coating to be applied. A generally conforming elastomeric mask is then disposed within the thimble. The elastomeric mask has a circumferential lower shoulder near its tip, and an aperture in its tip that communicates with a source of pressure. The circumferential shoulder on the elastomeric mask is of appropriate diameter to engage the tapered thimble side wall and space the mask tip from the thimble bottom. This spacing forms a cavity. The cavity is vented by a longitudinal surface relief on the mask extending from the cavity to the top of the thimble. Pressurizing the cavity through the mask tip aperture moves the ink up to the mask shoulder and then up to the thimble top along the mask surface relief.

BRIEF DESCRIPTION OF THE DRAWING

Other objects, features and advantages of the invention will become apparent from the following description of preferred embodiments thereof and from the drawing, in which.

DESCRIPTION OF THE PREFERRED EMBODIMENTS

Figure 1:
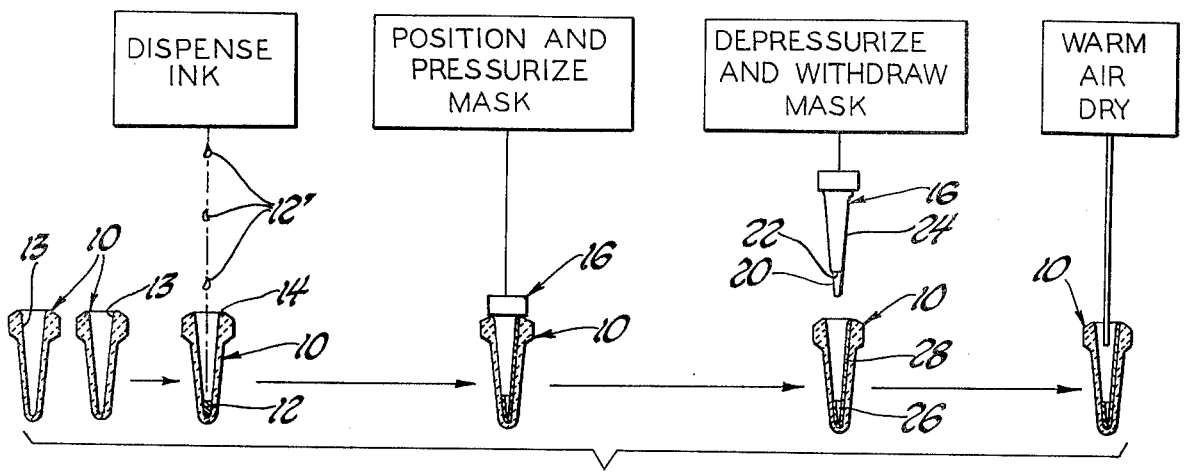
FIG. 1 diagrammatically shows the successive stages of my process for applying an ink to an interior of tapered zirconia thimbles.
Figure 2:
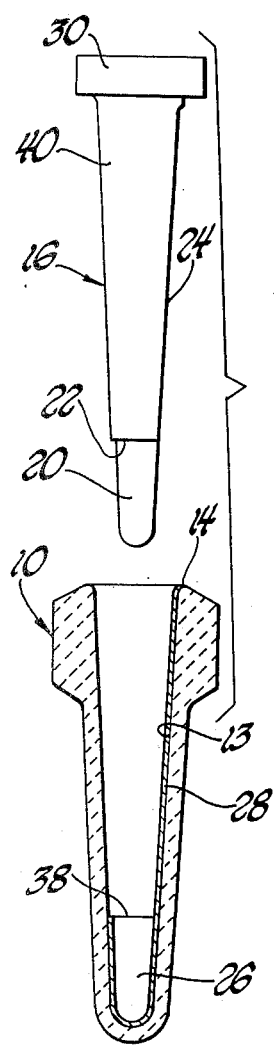
FIG. 2 shows an enlarged view of the mask and thimble shown in FIG. 1, the mask being shown in elevation and the thimble being shown in section.
Figure 3:
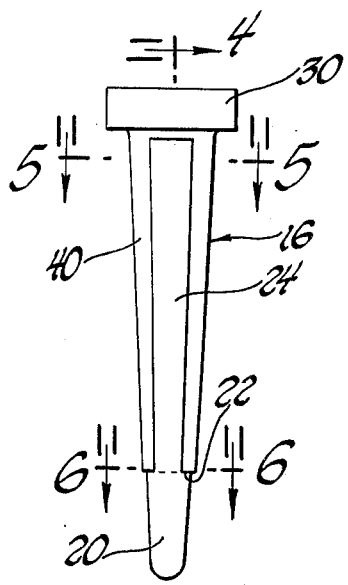
FIG. 3 shows a side view of the mask shown in FIG. 2.

Reference is now made to FIG. 1 which diagrammatically illustrates how the elastomeric mask of FIGS. 2-6 is used in this invention. It diagrammatically illustrates the various steps in the process of this invention by which a plurality of vitrified zirconia bodies 10 can be uniformly, rapidly and consistently coated. For convenience, the coating of only one of the thimbles is hereinafter described. In the initial step of the process, a predetermined and measured amount of platinum electrode ink 12 is dispensed within a thimble, being careful during the dispensing that ink drops 12' only contact portions of the cup interior that one desires coated.

A platinum ink that can be used in accordance with this invention would be predominantly a platinum powder containing about 0.5-5% by weight oxides and 20-45% by weight organic materials. Any of the normal and accepted commercially available inks can be used that provide porous conductive coatings after firing. A quantity is preferred that is sufficient to cover all parts of the interior area 13 to be coated, including upper portions of side wall stripe 26 but insufficient to overrun the top edge 14. An elastomeric tapered finger element 16 serves a unique masking function in this invention.

Figure 4:
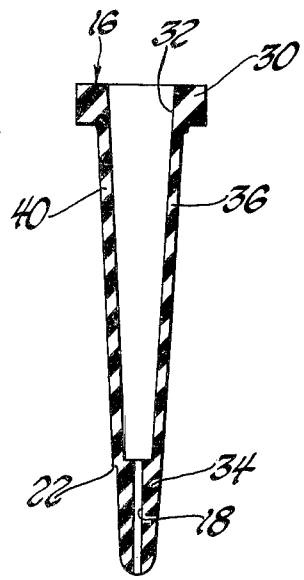
FIG. 4 shows a sectional view along the line 4—4 of FIG. 3.
Figure 5:
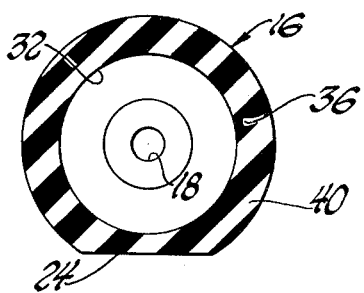
FIG. 5 shows a sectional view along the line 5—5 of FIG. 3.
Figure 6:
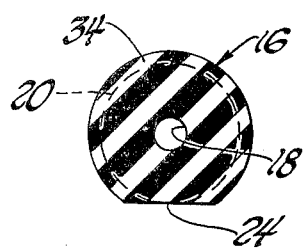
FIG. 6 shows a sectional view along the line 6—6 of FIG. 3.

Finger element 16 is hereinafter more fully described in connection with FIGS. 2-6. It is hollow and has a hole 18 in its lower end that communicates with its hollow interior, as shown in FIG. 4. The finger element 16 generally conforms to the interior of the thimbles 10 but has a reduced diameter portion 20 at its lower end that forms a circumferential external shoulder 22. A longitudinal external surface flat 24 on finger 16 extends along substantially the entire length of the finger, almost from its root, through shoulder 22 to intersect with the reduced diameter portion 20.

Referring back now to FIG. 1, finger 16 is nested within the thimble 10 with finger lower end 20 immersed in the premeasured quantity of platinum ink 12. When the finger is thus disposed, shoulder 22 circumferentially engages the side wall of the tapered interior thimble. Lower end 20 is thus spaced both radially and axially from adjacent portions of the thimble bottom. The spacing should not be significantly larger than the electrode coating thickness desired. The surface flat 24 similarly spaces a longitudinal portion of the finger from a corresponding longitudinal portion of the thimble interior side wall. When the finger 16 is sealed within the thimble, the ink 12 does not rise above shoulder 22. It is seated below shoulder 22 except for finger surface flat 24 and finger hole 18. If needed, the ink can be allowed to enter the finger interior to maintain it below shoulder 22 when seating the finger. It should also be mentioned that finger 16 is preferably tapered slightly less than the thimble interior 13 above shoulder 22 to facilitate better seating of shoulder 22 or the thimble interior side wall.

After the finger is so positioned, a gas pressure is applied to its hollow interior. Air can be used to provide this gas pressure. A sufficient pressure is applied to cause ink 12 to flow up along the outside of finger lower end 20 up to the shoulder 22. Ink 12 concurrently coats the adjacent bottom 26 of the thimble interior 13. It then flows up the finger surface flat 24 and forms stripe 28 on the thimble interior 13. The ink flows up the surface flat 24 under the gas pressure to the upper edge 14 of the thimble. As hereinbefore mentioned, the premeasured quantity of ink 12 is not sufficient to allow the ink 12 to run over the upper edge 14 of the thimble 10. In general, a pressure of about 20 to 40 psi is contemplated for use with thimbles and finger masks such as described herein. However, it should be recognized that other pressures could be used and may even be preferred if dimensions, inks, etc., are changed. I prefer to use not much more pressure than that needed to urge the ink all the way up to the top 14 of the thimble 10. When the ink 12 reaches the top 14 of the thimble 10, a vent path for the pressurizing air is formed, which may even provide a wiping or smoothing action on the ink. In any event, after the ink flows to the top of stripe 28 and air flows out the top of the passage formed by surface flat 24, the application of the pressure can be discontinued. The finger is then withdrawn from the thimble interior. The finger is obviously withdrawn coaxially from the thimble, and without rotation. The resultant coating is smooth and predetermined in area and thickness.

Warm, dry air is then blown into the thimble interior for about 10-20 minutes to dry the coating for subsequent conventional firing. It is fired to remove the temporary binders and the like and produce a porous electrode for use as a reference air electrode. The coated thimble is then dried and then fired. It can be dried by blowing clean, warm air, i.e. 38°-150° C., preferably 150° C., through it or by means of an infrared heater. It can also be dried in an oven but this is not preferred. In essence, any of the normal and accepted drying practices previously used can still be used with this invention. Analogously, this invention does not make firing of the coating any more critical either. It can be fired in the usual manner. For example, a six hour firing schedule can be used, in which the thimble is placed in a cold muffle furnace. The furnace is then heated to 1000° C., using an air atmosphere, and held there for 1-1½ hours. The furnace heating is then discontinued and the thimble left in the furnace for cooling to lower temperature. When the furnace has cooled to below 400° C., preferably below 200° C., the thimble is removed. If desired, the thimble can be inverted for drying after the finger mask is withdrawn, and completely dried while inverted. This, of course, will depend upon such factors as the coating thickness profile desired along the length of the thimble exterior, the viscosity of the particular ink used, the rate of drying used, etc. Also, to obtain the desired coating profile, it may be desired to invert the thimble for only a part of the time during which it is dried. I prefer to dry in such a manner as to prevent any substantial running of electrode ink back down to the bottom of the thimble. Generally, this can lead to blistering of the fired coating.

The coating process of this invention is made easy by special features incorporated in the elastomeric finger mask 16. It is shown enlarged in FIGS. 2-6. As previously mentioned, it includes a reduced diameter portion 20 at its lower end, a circumferential shoulder 22 and a linear axial surface flat 24 extending through the shoulder up to the upper end of the finger. The upper end of the finger has an enlarged portion 30 to facilitate attachment to a pressurizing means, support means and the like. The finger is hollow and has openings 32 and 18 at its upper and lower ends communicating with its hollow interior. The hollow interior forms an internal passage that communicates openings 32 and 18.

The circumferential shoulder 22 has a diameter at least as large as the corresponding part of the largest zirconia thimble variation which is expected to be encountered. If desired, it may be made a millimeter or so larger, but this may increase wear and produce associated problems. When the elastomeric mask is seated within the zirconia thimble 10, the shoulder 22 seats radially against the interior 13 of the thimble. This provides a cavity thereunder. The reduced diameter portion 20 of finger 16 below the shoulder corresponds roughly to the inner contour of the thimble but is spaced approximately 0.013-0.038 cm away from the inner surface of the thimble. However, at the extreme lower end of the finger surrounding finger lower aperture 18, it may be desired to increase the spacing to about 0.05 cm. It may even develop that very wide spacings between the finger end and the thimble bottom can be used, and that it may not even be necessary to initially immerse the finger end into a pool of ink 12. In any event, the wall 34 of finger 16 in lower portion 20 is significantly thicker than the finger wall 36 above shoulder 22. Lower wall 34 is thick enough that lower portion 20 will not appreciably distort when the finger is seated or the air pressure is applied to force the ink 12 up to the thimble top edge. Thus, finger-thimble spacing below the shoulder stays substantially constant once the finger is seated and air pressure is applied.

The finger wall 36 above shoulder 22, conversely, is preferably significantly thinner than wall thickness below the shoulder. This seems to aid in obtaining better definition on stripe 28. Why this occurs is not understood clearly. It may be that the thinner upper wall resists deformation less, so that it radially expands, under the force seating it in thimble 10 and the gas pressure applied within finger 16. If so, finger 16 would have a wider tolerance to thimble variations such as are attributable to different shrinkages during firing. In any event, finger wall 36 is preferably uniform in thickness along its length. The outer surface 40 of finger 16 is tapered slightly less than the adjacent interior 13 of thimble 10. In other words, the interior of thimble 10 decreases in diameter from top to bottom more than outer surface 40 of the finger does. Hence, shoulder 22 can seat tightly around the circumference of finger interior 13 when finger 16 is nested in the thimble. Also, it will part from the electrode stripe 28 more readily after the stripe is printed and still wet, and provide better edge definition for the wet ink. A difference of only 8-15 minutes in taper between the finger and thimble is all that is needed to provide these results. A greater taper difference may require that finger wall 36 be thinner and/or made of a softer rubber, and thus be not as durable.

The diameter of shoulder 22 is of a dimension that will rapidly engage the interior 13 of thimble 10 and seat thereon before reduced diameter portion 20 touches the bottom of the thimble. Hence the diameter of shoulder 22 is set to space the bottom of the finger and the thimble at least as far apart as the side wall of reduced diameter portion 20 and the thimble, and preferably considerably wider to provide a margin of tolerance. The wider the tolerance desired, the wider the bottom spacing used. As previously mentioned, a bottom spacing up to 0.05 cm can be used. Also, shoulder 22 alone can be used as a stop or a supplementary stop means may be provided. I prefer to use no supplementary stop means.

The surface flat 24 is equivalent to a 0.025 cm deep groove along the surface of the finger above shoulder 22. Both provide a longitudinal surface relief. The simple surface flat shown is preferred over a recessed longitudinal groove because the surface flat can be easily provided when the finger is molded. As with spacing of the lower portion 20 and the thimble, groove depth can vary from 0.013 to 0.038 cm, and even up to 0.05 cm. In the example shown here, it smoothly intersects the reduced diameter portion 20 of finger 16. However, that is not necessary. One may prefer a shallower or deeper groove. The preferred depths will be a matter of choice, depending on factors such as electrode characteristics desired, size of the thimble, viscosity of the ink, etc. The preferred thickness that is desired for upper wall 36 will be a function of a plurality of factors, including durometer of the elastomer used for finger 16, the actual size of the finger and thimble, the viscosity of the ink used, the relative difference in taper, etc. Accordingly, the finger can be varied somewhat from the specific example hereinafter disclosed.

In one specific example of this invention, a vitrified zirconia thimble of the configuration shown in the drawing was coated. The thimble is of zirconia stabilized partially or fully in its cubic crystalline form. The thimble 10 has the following nominal dimensions. However, it must be recognized that these dimensions can vary from 1.5% to 2.5%, due to nonuniform and inconsistent shrinkage during firing. The thimble is approximately 3.66 cm long and has an outer diameter of approximately 1.32 cm on its flange. Immediately below the flange it has an outer diameter of approximately 0.82 cm. Wall thickness diminishes gradually from about 0.178 cm in the area immediately below the flange to approximately 0.076 cm at the thimble bottom. The top of the thimble has an inner diameter of about 0.55 cm immediately below the radius on its top edge 14. It has a diameter of about 0.41 cm in the area where the top edge 38 of the inner electrode is formed. The distance between the top edge of the electrode area and the bottom interior of the thimble is approximately 1.02 cm.

For such a thimble, the mask can be formed of a urethane elastomer having the following physical characteristics: Tensile strength 3300 psi, 80 percent elongation, tear strength 400 PLI (DIEC), shrinkage 0.001 inches/inch, specific gravity 1.08, hardness 55-65 Shore D scale. One such elastomer that can be used is HD 0146, a urethane elastomer obtainable from Hysol Division of the Dexter Corporation. However, any of a wide variety of elastomers can be used for finger 16. The total length of finger 16 is 5.38 cm. This includes a flange 30 about 1.3 cm long, an upper portion 40 above shoulder 22 about 2.92 cm long, and portion 20 below shoulder 22 about 1.4 cm long. The diameter of flange 30 is approximately 1.9 cm. Immediately below the radius under flange 30, finger 16 has an outer diameter of about 0.58 cm. The bottom of flange 30 is spaced about 0.57 cm above the upper edge of the thimble when the mask is nested within the thimble.

The interior taper on thimble 10 is about 1 degree—41 minutes. The taper on finger 16 is about 1 degree—33 minutes. The diameter of finger 16 in the area corresponding to the top of the thimble is about 0.556 cm. Shoulder 22 has an outer diameter of about 0.417 cm. The width of shoulder 22 is about 0.254 cm. This produces a 0.254 cm spacing between the side walls of the mask and the thimble below shoulder 22. The linear axially extending surface flat 24 forms a 0.305 cm wide groove about 0.254 cm deep along the finger. Surface flat 24 smoothly intersects the reduced diameter lower portion 20. Finger wall 36 above shoulder 22 is about 0.064 cm thick. About 0.152 cm above the shoulder 22 it increases to about 0.102 cm.

The interior of finger 16 is tapered above the shoulder to provide the constant wall thickness. However, the finger interior is not tapered in its narrower diameter lower portion. Consequently, the wall thickness is not constant and decreases slightly, to about 0.089 cm immediately above the rounded portion at the lower end of the mask. It is not critical as to whether there is or is not a taper in thickness of the lower wall 34. However, what is important is that wall 34 have sufficient thickness to resist expansion under the pressures used to force the platinum ink along the groove formed by the surface flat 24. Analogously, the lower end 20 of finger 16 does not have to be spaced less than 0.038 cm from the bottom of the thimble. A larger spacing is permissible, particularly where thimble interior diameter variations are larger. Air pressure applied inside the finger 16 apparently produces an air jet from finger opening 18. The air jet moves the ink 12 up the sides of the thimble to shoulder 22, where it fills the lower end of the air vent formed by surface flat 24. The ink fills the cavity around shoulder 22 and is forced by air pressure along surface flat 24 up to the top 14 of the thimble. Concurrently, upper portion 40 of the finger radially engages thimble interior 13 tightly enough to seal the longitudinal edges of surface flat 24. As previously mentioned, only enough ink is predeposited to form the top of stripe 28. When the ink reaches the top of the thimble, there is substantially no excess ink left. It is all coated on the related passage side walls, which vents the coating cavity to the atmosphere. The flow of air is then discontinued and the finger axially withdrawn. The coated thimble is then dried and fired as hereinbefore described. If the axial upper face 14 of the thimble is to also be coated with ink, this is preferably done in a separate operation, before coating 26–28 is fired. Then only one firing is needed.

The embodiments of the invention in which an exclusive property or privilege is claimed are defined as follows:

1. A process for rapidly and consistently selectively applying a conductive coating liquid to the interior bottom and side wall of tapered ceramic cups, the method comprising the steps of:

dispensing a metered quantity of the conductive coating liquid into the cup interior directly onto a portion of the bottom to be coated, said quantity not being significantly greater than that needed to coat a preselected portion of the cup interior to be exposed within a coating recess;

nesting a tapered masking element within the cup to seat an element shoulder on the cup side wall and axially space said element within a predetermined distance from said cup bottom, said element having a taper somewhat less than that of the cup interior and said element shoulder being provided by a reduced diameter end on said element, said reduced diameter end coacting with the cup interior to provide a recess corresponding to the area of the cup bottom to be selectively coated, said element also having an aperture in said end, means for communicating said aperture with a source of pressure and means for venting said recess from said shoulder;

applying a gas under pressure to said recess through said element aperture to move said liquid up to said shoulder and coat all portions of the cup interior exposed within the recess;

continuing to apply said gas under pressure until a gas flow from said aperture through said recess commences; and axially withdrawing said element from said cup, whereby a smooth coating is applied to the cup interior.

2. The method of rapidly and reproducibly forming an interior electrode coating on the bottom and side of tapered vitrified zirconia thimbles for an exhaust gas oxygen sensor, said coating having a predetermined weight and electrical resistance, said method comprising the steps of:

dispensing a premeasured quantity of a conductive ink into the bottom of the thimble to be coated;

axially inserting an elastomeric finger into the thimble, said finger being tapered slightly less than said thimble and having a smaller diameter end portion which forms a circumferential shoulder, a longitudinal surface relief on said finger extending from said shoulder to a finger root portion not recessable in said thimble, said finger having an aperture in said end and means for communicating it with a source of gas pressure;

seating said finger in said thimble to immerse only said end in said ink and form a predetermined coating cavity having a longitudinal venting recess;

applying a gas pressure to said aperture to flow the conductive ink throughout said cavity and up said longitudinal venting recess, apply substantially all said ink to walls forming said cavity and recess, and then flow gas through said cavity and recess; and removing the gas pressure and axially withdrawing the finger from the thimble, whereby the thimble has a smooth interior coating of predetermined weight and electrical resistance selectively applied to its interior bottom and side.

3. A mask for forming an electrode coating selectively onto the interior bottom and side of a ceramic tapered cup, said mask comprising a tapered elastomeric finger having an outer configuration generally nestable within the cup interior, a reduced diameter end portion on said finger corresponding to the area of the cup bottom to be coated, a circumferential sealing means on said finger adjacent said reduced diameter end portion, linear recess means on the outer surface of the finger axially extending through said sealing means from said reduced diameter portion and providing a gas vent and a side wall mask, said circumferential sealing means being of a diameter to space the finger end a predetermined distance from the cup bottom, said finger outer surface adjacent said linear recess means being tapered less than the cup interior, an aperture in the finger end for applying a jet of a gas to a liquid in said cup below said sealing means, passage means in said finger for communicating said aperture with a source of gas pressure, body wall thickness below said sealing means being thick enough to resist significant deformation when said pressure is applied, whereby a smooth predetermined continuous coating of said liquid can be consistently selectively applied to the cup bottom and side.

4. An elastomeric mask for forming an electrode coating selectively to the interior bottom and side of zirconia solid electrolyte tapered cups, said mask comprising a tapered hollow elastomeric body having an outer configuration generally nestable within the interior of said cup, a reduced diameter end portion on said body providing an integral circumferential shoulder and corresponding to the area of the cup bottom to be coated, said end portion adapted to be immersed in a pool of fluid electrode material disposed in said cup below said shoulder, a longitudinal flat on the outer surface of the body for venting said shoulder and providing a side wall stripe mask, said shoulder of a diameter effective to radially engage the tapered cup interior and axially space said body end and cup bottom a predetermined distance apart, body portions radial to said surface flat being tapered less than said cup interior, an aperture in said body end communicating with said body hollow interior for applying a pressurized gas to said pool of electrode material below its upper surface, body wall thickness below said shoulder being thick enough to resist significant deformation under said shoulder engagement and pressurized gas, body wall thickness above said shoulder being thinner so as not to resist deformation as much as above said shoulder during said shoulder engagement and said pressurized gas, whereby a smooth predetermined continuous coating of said electrode material can be consistently selectively applied to said cup interiors.

5. A process of applying a conductive coating to the tapered interior cavity surface of a zirconia thimble for an automotive exhaust gas oxygen sensor comprising the steps of:

depositing a metered quantity of liquid platinum ink containing platinum powder and about 0.5-5% by weight oxides and 20-45% by weight organic material into the zirconia thimble cavity with the latter being in upwardly concave orientation, forming a liquid pool at the bottom of the cavity;

while the ink is still liquid and the cavity in substantially the same orientation, inserting an elastomeric hollow tapered mask into said cavity, the hollow mask having a substantially uniform wall thickness for a major part of its axial length towards its tip except for an axially extending exterior recess along said part, and a relatively thicker wall and a reduced diameter for the remainder of its axial length, the mask when seated in said cavity forming a space in relation to the cavity which extends over the entire surface of the cavity for said remainder of mask axial length and which further extends over a fragment of the surface of the cavity exposed to said axially extending recess, said further extension being vented to relieve a gas pressure applied to said space;

applying fluid pressure to said metered ink quantity in said cavity through the interior of the mask, whereby the ink coats said cavity entire surface adjacent said mask remainder portion and coats said cavity fragment surface along said mask axial recess; and terminating the pressure and withdrawing the mask.

6. A process of applying a conductive coating to the tapered interior cavity surface of a zirconia thimble for an automotive exhaust gas oxygen sensor comprising the steps of:

depositing a metered quantity of liquid platinum ink containing platinum powder and about 0.5-5% by weight oxides and 20-45% by weight organic liquid-forming material into the cavity with the latter being in upwardly concave orientation, forming a viscous liquid pool at the bottom of the cavity;

while the ink is still liquid and the cavity in substantially the same orientation, inserting an elastomeric hollow tapered mask into said cavity, the mask forming a predetermined peripheral seal within the cavity for a space in relation to the cavity which extends over the entire surface of the cavity for a predetermined axial length upwardly from the bottom of the cavity and which further extends, in a fragment of the periphery of the cavity for the remaining axial length thereof, the space along said periphery fragment providing a vent for fluid pressure applied to said space;

applying a gas pressure to the space from the mask tip, whereby the ink expands out from said pool to coat said entire surface and periphery fragment;

terminating gas flow after the measured quantity of ink has been distributed within the cavity and gas flow exhausts through said vent space;

withdrawing the mask; and drying the ink coat on said surface while preventing any substantial repooling of the ink in the cavity bottom.

7. A process for selectively applying a viscous conductive coating liquid to the interior bottom and side wall of tapered ceramic cups, the method comprising the steps of:

dispensing a metered quantity of the conductive coating liquid into the cup interior to form a pool on the bottom portion to be coated, said quantity not being significantly greater than that needed to coat a preselected portion of the cup interior;

nesting a generally conforming masking element within the cup, said masking element having means coacting with the cup interior to provide a recess corresponding to the portions of the cup interior surface to be selectively coated, said element also having means for applying gas pressure to said recess at said cup bottom and means for venting said recess;

applying said gas pressure to said recess at said cup bottom and to move said conductive coating liquid throughout said recess and coat all portions of the cup interior exposed therewithin, whereby substantially all of said metered quantity of coating liquid is selectively applied to walls defining said recess;

discontinuing said gas pressure after gas begins to exhaust through said recess venting means;

withdrawing said element from said cup; and drying said coating without permitting any significant redistribution of said liquid.

* * * * *